United States Patent [19]

Madison

[11] Patent Number: Plant 6,973

[45] Date of Patent: Aug. 8, 1989

[54] WALNUT TREE NAMED VESTER

[76] Inventor: Dennis N. Madison, 23672 Maple La., Romulus, Mich. 48174

[21] Appl. No.: 244,036

[22] Filed: Sep. 14, 1988

[51] Int. Cl.[4] ..... A01H 5/00

[52] U.S. Cl. ..... Plt./32

[58] Field of Search ..... Plt./32

*Primary Examiner*—Robert E. Bagwill

*Attorney, Agent, or Firm*—Joseph J. Goluban

[57] ABSTRACT

A new and distinct variety of Persian Walnut Tree having an abundance of fruit particularly when young. The nuts are of an oblate shape and have a high percentage of sweet mild kernels.

2 Drawing Sheets

BACKGROUND OF THE INVENTION

This invention pertains to a new and distinct variety of Persian walnut tree.

The tree grew from one of the seedlings obtained from crossings of pollen by me, in the garden of property I owned in Romulus, Mich., U.S.A. As the tree developed and began to bear fruit its improved characteristics became more and more evident. My interest and experience with the development of nut trees led me to realize that it was a unique and distinct development.

REPRODUCTION

Subsequently, I asexually reproduced the plant by grafting on to an unpatented black walnut stock. Thereafter, I observed the development and growth of the clone, its fruiting, resistance to cold, and other characteristics by which its value and its truthfulness to the original tree could be judged.

DESCRIPTION OF PRIOR ART AND DEVELOPMENT

The instant plant is the result of deliberate breeding to achieve a self-pollenating thinner shelled, heavy bearing, early ripening Carpathian, i.e., a Juglans regia.

The male parent is a Hansen Juglans regia. The Hansen was discovered and first grafted in 1939 by Sylvester Shessler. It was named Hansen as it was growing in a portion of the farm of Awalt Hansen. Its seed was planted about 1921. The source of the seed is unknown. Hansen is not patented but is widely planted.

The female parent is Merkel Juglans regia. Merkel was planted in 1936 by Henry Merkel from seed received from the Wisconsin Horticultural Society that came from the Carpathian mountains of Southern Poland. The seed was likely from among nuts collected by Rev. Crath of Ontario, Canada during his visits to Eastern Europe in 1932 through 1936.

Merkel was discovered and first grafted by myself in 1963. Merkel is not patented but is distributed throughout most of the Northern United States.

I crossed Merkel with pollen from Hansen in May of 1973, and this resulted in nuts which were planted in 1974. One of these nuts grew into the tree, the plant, of the instant invention.

I asexually reproduced the tree by grafting a scion thereof onto a large Juglans nigra, black walnut tree in June 1984. I designated the tree as No. U81227P-US. The result is true to the parent in all respects including branching, leaves, flowering, fruits and the trees' general appearance and shape.

SUMMARY OF INVENTION

The Walnut Tree herein claimed as a new and patentable variety combines the good qualities of both its parents. Further, it is heavier bearing and ripens earlier in addition to having thinner shelled nuts of high meat quality. Furthermore it bears fruit in lateral buds as well as on the terminals.

DESCRIPTION OF THE INVENTION

Figure 1:
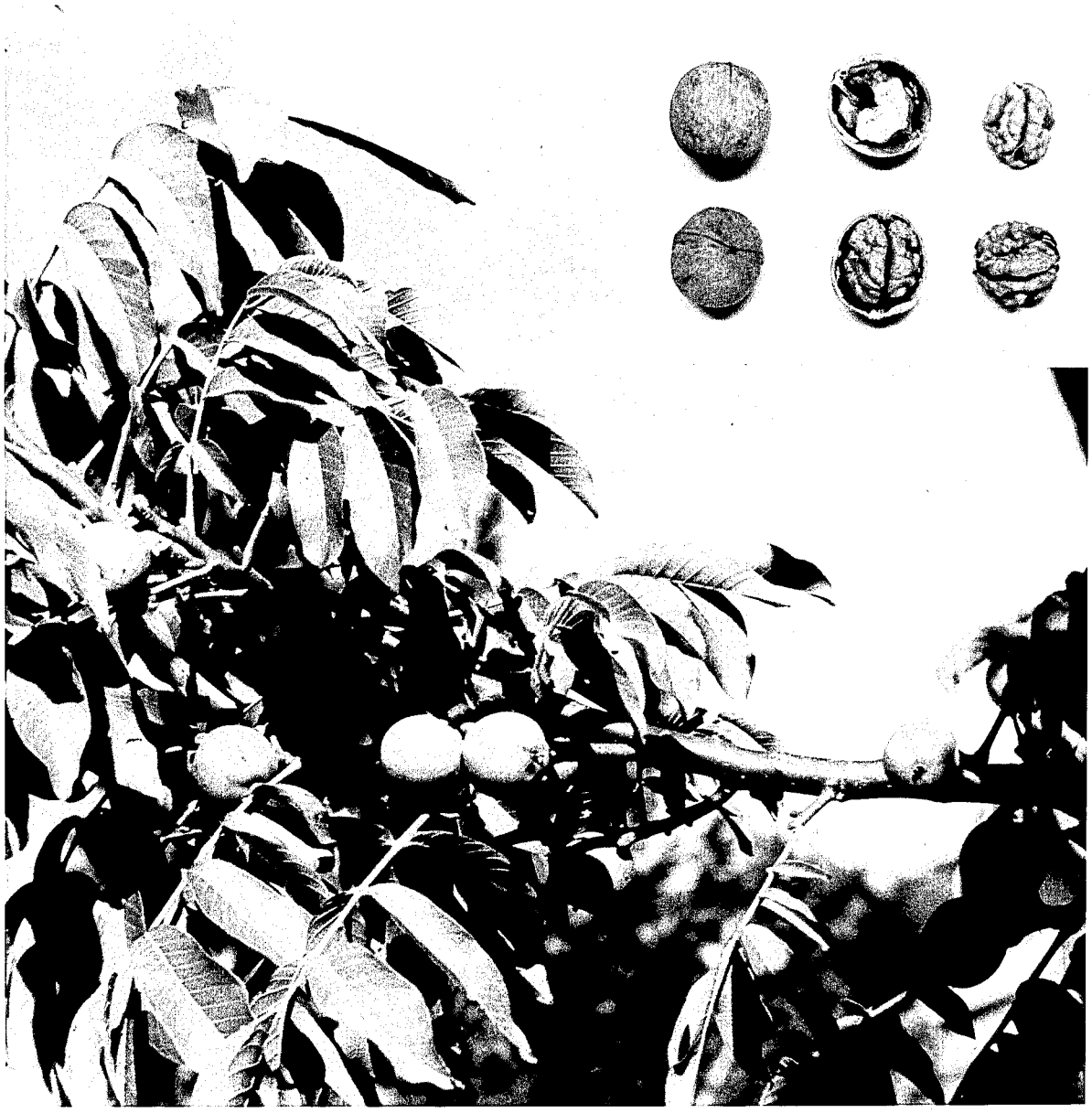
FIG. 1 shows the bearing of fruit on laterals as well as the foliage of the new variety, together with nuts in the shell, nuts with one half of their shells removed with one of the latter having a kernel in cross section, and two kernals without shells.
Figure 2:
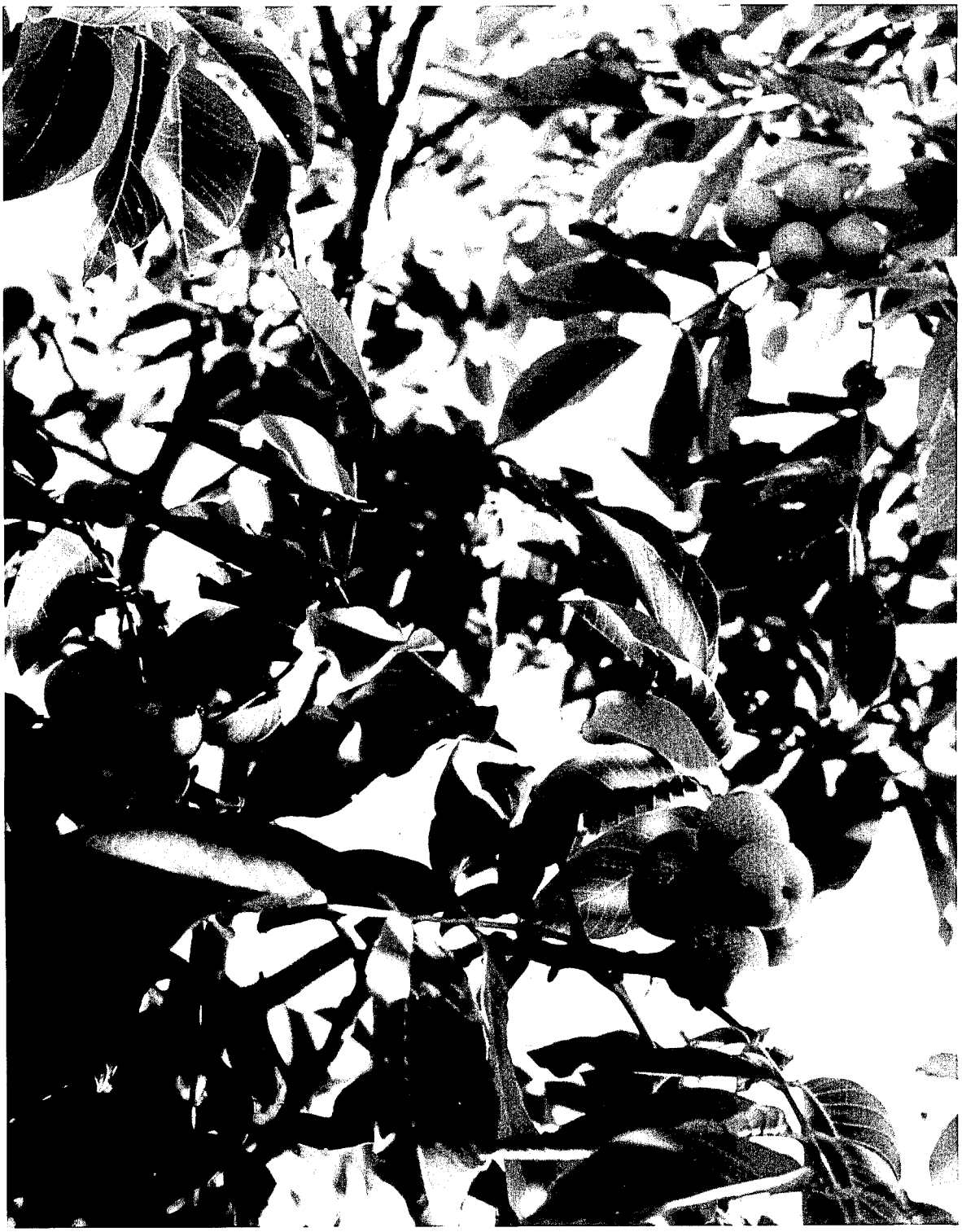
FIG. 2 shows the bearing on terminals.

The Walnut Tree is of a medium height and breadth. It produces a moderate to dense foliage. It grows vigorously producing spreading branches and a liberal number of buds and laterals. It is about as broad as it is high. The leaves are ovate to eliptic in shape, and they number about 7 to 9 to a leaflet. They are abundant, producing a shady tree, but one that at the same time is relatively light and airy as contrasted to those having a density of the nature of a tree such as a Beech, for example.

The tree is attractive and makes an excellent shade tree or ornamental tree.

The fruit is small to medium in size.

Its most recent growing produced nuts which in competition type inspection were described as follows:

Size: Small to Medium. 54 per pound.

Shape: Roundish oblate.

Shell: Yellowish brown covered with a network of shallow veins converging at the apex, very thin, translucent where diaphragm tears away from shell midway between sutures.

Base: Smooth except for longitudinal lines. Sutures slightly ribbed at equator with variable pits.

Flange: Thin and well sealed.

Diaphragm: Almost weakly shoulded, thin, yielding, rarely persistent.

Kernel: Full, plump, convolutions moderate and even. Pellicle light golden brown, semi-glossy to glossy, slightly astringent, veins absent or inconspicuous, flesh oily and rich. Flavor mild and sweet. Quality good.

Percentage: 62% kernel.

The production of fruit on the laterals is a distinct advantage particularly in the early years of the tree. The quantity is much greater than if nuts occurred only on the terminals as is customary with its parents. The terminals have up to five nuts per cluster further enhancing the out-put. In addition, the nuts are of high quality. The fruit also ripens early. In Romulus, Mich. the fruit ripens in the last week of August and the first week of September. The foliage and blossoms do not show until early May, but the harvest begins well within the growing period in Southern Michigan. The tree is self-pollenating.

Due to the smaller size, the nuts are not competitive with the walnuts of the larger presently available commercial sizes in California. The tree, is however, advantageously hardy and not only suitable for an ornamental, but in addition produces a nut well worth harvesting and using for local purposes. It is very suitable for decoration of cakes, etc. It has a desirable flavor.

The nuts are easily recovered from the ground. Yet the shells are relatively thin and easy to open without damage to the kernel. In addition, the tree produces a bountiful harvest.

The tree appears to be as resistant as it forebears to disease and insects. It can be grafted or budded onto black walnut seedlings.

It will be understood that the tree and its fruit can vary somewhat due to differences in climate, topography, and soil conditions, under which it is grown.

I claim:

1. A new and distinct variety of cultivar of Persian Walnut Tree as herein described and illustrated and characterized by being of a medium size, having a moderate to dense foliage, a vigorous growth with spreading branches producing a tree about as broad as it is high, elliptical leaves about 7 to 9 per lateral, that flowers abundantly on both laterals and terminals, produces a very early crop of abundant fruit on both laterals and terminals with some large clusters, with shells which are thin and smooth and well sealed and of a rounded oblate shape and a yellowish brown color, and which are small to medium in size with a high percentage of full plump kernels of a mild sweet taste and good quality, the tree being hardy and resistant to cold.

* * * * *